United States Patent [19]

Dietrich et al.

[11] 4,225,404

[45] Sep. 30, 1980

[54] PERFLUOROOLEFIN AND PERFLUOROPARAFFIN MIXTURE AND PROCESS FOR MAKING SAME

[75] Inventors: Peter Dietrich; Günter Engler, both of Berlin; Armin Ferse, Dresden, all of German Democratic Rep.; Harald Grimm, deceased, late of Dresden, German Democratic Rep., by Ingrid A. Grimm, heiress; Udo Gross, Berlin, German Democratic Rep.; Dietmar Handte, Rupperdorf, German Democratic Rep.; Klaus Lunkwitz, Dresden, German Democratic Rep.; Ulrich Müller, Berlin, German Democratic Rep.; Dietrich Prescher, Berlin, German Democratic Rep.; Jürgen Schulze, Berlin, German Democratic Rep.

[73] Assignee: Akademie der Wissenschaften der DDR, Berlin, German Democratic Rep.

[21] Appl. No.: 912,038

[22] Filed: Aug. 24, 1978

[51] Int. Cl.$^2$ .......................... B01J 1/10; C07C 21/18
[52] U.S. Cl. ....................... 204/163 R; 204/158 HE; 204/163 HE; 252/1; 252/2; 252/63; 260/653.1 R
[58] Field of Search ..... 204/163 R, 163 HE, 158 HE, 204/159.2; 260/653.1 R; 252/1, 2, 63

[56] References Cited

U.S. PATENT DOCUMENTS

3,062,794  11/1962  Iserson et al. ................... 204/163 R

FOREIGN PATENT DOCUMENTS

| | | | |
|---|---|---|---|
| 668929 | 8/1963 | Canada ............................. | 260/653.1 R |
| 117705 | 9/1975 | Japan ................................ | 260/653.1 R |
| 1302350 | 1/1973 | United Kingdom ............. | 260/653.1 R |

OTHER PUBLICATIONS

Hudlicky, Chemistry of Organic Fluorine Compounds, The MacMillan Company, New York, 1962, pp. 273 to 276.

*Primary Examiner*—Leland A. Sebastian
*Attorney, Agent, or Firm*—Michael J. Striker

[57] ABSTRACT

Straight chain perfluoroolefins compounds of medium length with terminal or double bonds and a minor proportion of trifluoromethyl side chains or mixtures of such perfluoroolefins with perfluoro paraffins of equal chain length and corresponding structure, the perfluoroolefins being present in the mixture in an amount of 40 to 70%. The compounds are valuable as highly reactive intermediate products in the production of surface active agents. The compounds are made by subjecting a highly fluorinated organic compound to degradation by means of a high energy radiation of a density of 0.3 to 3.0 W/cm$^2$ effected in a radiation chamber which has been subjected to a preceding rinsing with an inert gas or with a monomeric highly fluorinated organic compound.

11 Claims, No Drawings

PERFLUOROOLEFIN AND PERFLUOROPARAFFIN MIXTURE AND PROCESS FOR MAKING SAME

BACKGROUND OF THE INVENTION

The invention relates to straight chain perfluoroolefins of medium chain length with terminal or internal double bonds which are valuable as highly reactive intermediate products in the production of surface active agents.

Among the straight chain perfluorinated olefins those are known which have a chain length increasing up to $C_9$. These short chain perfluoroolefins have been widely investigated regarding their properties. However, there is a scarcity of data regarding the chemical properties of the homologs with a carbon chain of $C_7$ to $C_9$ because of the difficulties in producing these compounds. The short chain perfluorinated olefins can easily be polymerized. They can also be converted to oligomers ionically, or can be reacted by means of nucleophilic reaction. They are mainly used as starting products for making fluoropolymers and constitute intermediate products, for instance in the production of fire extinguishing agents and of propellant gases.

There have also already been prepared highly branched perfluoroolefins such as the perfluoro-4-ethyl-3,4-dimethyl-hex-cis-2-ene which latter have a chain length of 6 to 7 carbon atoms and are highly reactive to nucleophilic reaction components because of their branched structure and the resulting negative induction effect. They are used as starting products or intermediate products for making surface active agents.

It is also known that perfluoroolefins can be obtained by thermal decomposition of dry alkali salts of perfluorinated alkyl carboxylic acids [J. D. La Zerte, L. J. Hals, T. S. Reid, G. H. Smith, Journal American Chemical Society 75 (1953) 4525]. This method is, however, not suitable for large scale operations for economic reasons.

A further process for obtaining perfluoroolefins is the ionic conversion to oligomers of tetrafluoroethylene (British Pat. No. 1,082,127) in which case highly branched perfluorinated olefins such as the perfluoro-4-ethyl-3,4-dimethyl-hex-cis-2-ene are formed. These reactions are carried out on an industrial scale in batch operations in a steel autoclave under exclusion of oxygen and humidity in an anhydrous organic solvent in the presence of the very expensive cesium fluoride. The formed perfluorinated oligomerolefin $C_{10}F_{20}$ is obtained after separating off the byproducts formed by distillation in yields of between 50 and 60%. This process requires the observation of specific safety procedures in order to avoid an undesirable spontaneous exothermic polymerization when working under pressure with the tetrafluoroethylene.

It has also become known from German Patent Nos. 112,589 and 112,197 that highly fluorinated polymers can be degraded by chemical radiation methods. The thusly formed mixture of various degradation products is not defined further chemically. A disadvantage is that the degradation products must be removed from the reaction zone by means of a carrier gas followed by isolation thereof from the carrier gas by fractionation techniques in order to obtain their separation. The carrier gas stream hereby also entrains the insufficiently degraded polymers as a fine dust. Further complete isolation of the degradation products, because of the high steam pressures, is possible only by application of expensive adsorption batteries or low temperatures.

It is therefore an object of the present invention to form straight chain perfluoroolefins of medium chain lengths which are distinguished structurally and by their composition from the prior art perfluoroolefins and which can be used as intermediate or starting products for making surface active agents.

SUMMARY OF THE INVENTION

The above objects are achieved by straight chain perfluoroolefin compounds of medium chain length which have terminal or internal double bonds and include a minor proportion of trifluoromethyl side chains. The compounds may also be present in a mixture of these perfluoroolefins with perfluoroparaffins of equal chain lengths and corresponding structure in which case the perfluoroolefins are present in the mixture in an amount of 40 to 70%.

The invention also embraces a process for making the compounds by subjecting a highly fluorinated organic compound to degradation by means of a high energy radiation of a density of 0.3 to 3.0 W/cm$^2$ effected in a radiation chamber which has been subjected to a preceding rinsing with an inert gas or with a monomeric highly fluorinated organic compound.

The minor proportion of trifluoromethyl groups is $^{19}$F-NMR-spectroscopically determinable. The compounds have a characteristic $^{19}$F-NMR-fingerprint spectrum. When carrying out the degradation process the degraded products distil or sublime from the radiation chamber into the attached collector because of their own vapor pressure and are thus separated from the polymer portions.

DETAILS OF THE INVENTION AND PREFERRED EMBODIMENTS

As highly fluorinated organic starting products the following may for instance be used:

[1] Highly fluorinated polymers or oligomers and their derivatives such as polytetrafluoroethylene, perfluorocarbons of a molecular mass up to $10^7$, chlorine containing fluorocarbons and polyvinylidenefluoride.

[2] Mixed polymerisates of tetrafluoroethylene with monomeric fluorinated compounds such as hexafluoropropene, chlorofluorethylene and unfluorinated compounds such as ethylene.

These polymers or mixed polymers can either be introduced directly as high molecular compounds into the radiation chamber, or they are formed therein by introducing the corresponding monomer.

The radiation chamber is rinsed prior to the commencement of the degradation with an inert gas such as nitrogen or argon. It is, however, also possible to use monomeric highly fluorinated organic compounds for this purpose.

The average molecular mass of the formed degradation products is controlled by the radiation temperature which is a result of the energy density.

It has been found that at an energy density in the range from 1.1 to 2.0 W/cm$^2$ the proportion of desirable straight chain perfluorinated olefins of medium chain length particularly of 6 to 14 carbon atoms is particularly high.

The solid perfluorinated paraffins and olefins of a chain length $>C_{14}$ which also occur can be circulated in case of a continuous process.

The gaseous perfluorinated paraffins and olefins can be further used in conventional methods.

The process is distinguished by the following features:

[1] The proportion of straight chain perfluorinated olefins of medium carbon lengths is relatively high.

[2] The perfluorinated olefin-paraffin mixtures which are obtained by fractionation are free of powdery insufficiently degraded polymer fractions.

[3] Without difficulty monomeric highly fluorinated compounds such as tetrafluoroethylene can be used as starting products.

The degradation products of 6 to 14 carbon atoms as they are obtained from polytetrafluoroethylene distil at 50° to 220° C. and include olefins with an internal (IR: 1730 cm$^{-1}$) and a terminal (IR: 1790 cm$^{-1}$) double bond.

The diolefin proportion is small. Depending on the radiation parameters, the proportion of terminal olefins can be varied to some extent. By means of the $^{19}$F-NMR-spectroscopy it is possible to determine the presence of small proportions of side chains (16.9 to 19.2 ppm and 4.28 to 6.96 ppm; low intensity; standard $CF_3CO_2H$).

As can be determined by IR-spectroscopic examination prior and after the reactions, the paraffin fraction is about 30 to 60%. The paraffin fraction of the formed mixtures does not affect the olefin reactions. After carrying out the functional reaction of the olefin portions the paraffin portion can be separated, for instance because of its low solubility and can be passed to a separate use. Perfluoroparaffins are themselves valuable compounds for chemical technology.

The products of the process of the invention are thermally stable and can be used as solvents, cooling agents and dielectrics.

The perfluoroolefins of the invention are important intermediate products which can be used for instance for making compounds which have surface active and/or hydrophobic and/or oleophobic properties.

The following examples will further illustrate the invention.

EXAMPLE 1

1000 g of polytetrafluoroethylene were subjected in a nitrogen rinsed reaction chamber to an electronic radiation of 0.9 MeV acceleration voltage and 2000 W (corresponding to an energy density of 1.33 W/cm$^2$). The degradation products were distilled from the radiation space and condensed in attached collectors. The reaction was complete after 2.5 hours. There were obtained 800 g of straight chain perfluorinated olefins and paraffins of a chain length between $C_6$ to $C_{25}$ which are free of any powdery polymers. 300 g of the product are present as straight chain perfluorinated olefins having a chain length between $C_6$ to $C_{14}$ while the remainder consists of liquids and solid perfluorinated paraffins and of perfluorinated olefins having a chain length $>C_{14}$. In addition, there were obtained 200 g of gaseous perfluorinated olefins and paraffins.

EXAMPLE 2

100 l tetrafluoroethylene per hour were subjected in a reaction space that had been rinsed with tetrafluoroethylene to an electronic radiation of a 1.0 MeV acceleration voltage and 3000 W (energy density 2.0 W/cm$^2$).

By immediate complete polymerization there was formed polytetrafluoroethylene which at once was degraded again to lower molecular fractions. These were condensed after distillation from the reaction space in the attached collectors. There were obtained per hour 330 g of straight chain perfluorinated olefins and paraffins having a chain length of between $C_6$ and $C_{25}$. Of these products 140 g were present as straight chain perfluorinated olefins having a chain length of $C_6$ to $C_{14}$. The remainder consisted of liquid and solid perfluorinated paraffins and of perfluorinated olefins having a chain length $>C_{14}$. There were obtained in addition 90 g of gaseous perfluorinated olefins and paraffins.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. Straight chain perfluoroolefin compounds of medium chain length having terminal double bonds and only a minor proportion of trifluoromethyl side chains per se or in admixture with perfluoroparaffins of equal chain length and corresponding structure, the perfluoroolefin compounds being present in such mixture in an amount of from 40 to 70%.

2. The perfluoroolefins of claim 1 which have a chain length of 6 to 14 carbon atoms.

3. A process for making straight chain perfluoroolefin compounds of medium chain length having terminal double bonds and only a minor proportion of trifluoromethyl side chains per se or in admixture with perfluoroparaffins of equal chain length and corresponding structure, the perfluoroolefin compounds being present in such mixture in an amount of from 40 to 70% which comprises subjecting a highly fluorinated organic compound to degradation by means of a high energy radiation of a density of 0.3 to 3.0 W/cm$^2$ in a radiation chamber which has been subjected to a preceding rinsing with an inert gas or with a monomeric highly fluorinated organic compound.

4. The process of claim 3 wherein the highly fluorinated organic starting compound has been produced from the corresponding monomer by radiation polymerization.

5. The process of claim 3 wherein the high energy radiation is an electron radiation.

6. The process of claim 3 wherein the highly fluorinated organic starting compounds are polymers of oligomers or derivatives thereof.

7. The process of claim 3 wherein the highly fluorinated organic starting compounds are mixed polymerisates.

8. The process of claim 3 wherein the highly fluorinated organic starting compounds in the form of polymerisates or mixed polymerisates are formed by introducing the corresponding monomers directly into said radiation chamber.

9. The process of claim 3 wherein the radiation chamber prior to said degradation is rinsed with nitrogen, argon or a gaseous perfluoroparaffin.

10. The process of claim 3 wherein the radiation chamber prior to said degradation is rinsed with a monomeric highly fluorinated organic compound.

11. The process of claim 3 wherein the density of the radiation is between about 1.1 and 2.0 W/cm$^2$.

* * * * *